United States Patent [19]

Campbell et al.

[11] Patent Number: 4,704,282

[45] Date of Patent: Nov. 3, 1987

[54] TRANSDERMAL THERAPEUTIC SYSTEM HAVING IMPROVED DELIVERY CHARACTERISTICS

[75] Inventors: Patricia S. Campbell, Palo Alto; James B. Eckenhoff, Los Altos, both of Calif.

[73] Assignee: Alza Corporation, Palo Alto, Calif.

[21] Appl. No.: 626,095

[22] Filed: Jun. 29, 1984

[51] Int. Cl.[4] ........................... A61K 9/22; A61K 9/26
[52] U.S. Cl. ........................... 424/449; 424/DIG. 14; 604/897; 514/953; 514/965
[58] Field of Search ................. 424/28, DIG. 14, 449; 604/897; 514/953, 965

[56] References Cited

U.S. PATENT DOCUMENTS

| | | | |
|---|---|---|---|
| 3,598,122 | 8/1971 | Zaffaroni | 424/28 |
| 3,742,951 | 7/1973 | Zaffaroni | 424/28 |
| 3,813,466 | 5/1974 | Anderson | 424/28 |
| 3,923,939 | 12/1975 | Baker et al. | 424/21 |
| 4,069,307 | 1/1978 | Higuchi et al. | 424/19 |
| 4,144,317 | 3/1979 | Higuchi et al. | 424/28 |
| 4,201,211 | 5/1980 | Chandrasekaran et al. | 424/28 |
| 4,243,656 | 1/1981 | Walliczek | 424/28 |
| 4,262,003 | 4/1981 | Urquhart et al. | 424/28 |
| 4,286,592 | 9/1981 | Chandrasekaran | 424/28 |
| 4,379,454 | 4/1983 | Campbell et al. | 604/897 |

FOREIGN PATENT DOCUMENTS

| | | | |
|---|---|---|---|
| 3424837 | 1/1986 | Fed. Rep. of Germany | 604/897 |
| 56-99410 | 8/1981 | Japan | 424/28 |
| 2030860 | 4/1980 | United Kingdom | 604/897 |
| 1594389 | 7/1981 | United Kingdom | 604/897 |
| 2086224 | 5/1982 | United Kingdom | 424/449 |

OTHER PUBLICATIONS

Ben Galim et al., "Topically Applied Testosterone and Phallic Growth", AM. J. Dis. Child., 134:296–298 (1980).
Jacobs et al., Topical Testosterone Therapy for Penile Growth, UROL, 6:708–710 (1975).
Klugo et al., "Response of Micropenis to Topical Testosterone and Gonadotropin", J. UROL, 119:667–668 (1978).

Primary Examiner—Ronald W. Griffin
Attorney, Agent, or Firm—Steven F. Stone; Edward L. Mandell; Shelley Precivale

[57] ABSTRACT

A transdermal therapeutic system using a subsaturated matrix is provided having improved approved release characteristics. Reinforcing means preferably in the form of a fabric are embedded in the upper surface of the subsaturated matrix. At least a portion of the reinforcing means is selected such that the active agent to be delivered to the skin has a solubility, $C_r$ therein which is lower than the initial solubility $C_o$ of the agent in the matrix. In addition, the relationship between the diffusion coefficients of the agent in the matrix $D_m$ and the portion of reinforcing means $D_r$ and the solubilities is given by the relationship: $D_r \cdot C_r < D_m \cdot C_o$. In operation the agent dissolved in the reinforcing means acts as a secondary reservoir improving the release characteristics of the system. Specific embodiments of the invention are particularly adapted for scrotal and labial delivery of drugs such as testosterone and progesterone.

43 Claims, 3 Drawing Figures

TRANSDERMAL THERAPEUTIC SYSTEM HAVING IMPROVED DELIVERY CHARACTERISTICS

FIELD OF THE INVENTION

This invention relates to the parenteral delivery of biologically active materials and more particularly to the delivery of such materials to the human body in therapeutic amounts through intact skin.

BACKGROUND OF THE INVENTION

Numerous devices are known to the art for delivering various drugs and other biologically active agents (hereinafter, "agent") through the skin, Representative U.S. Pat. Nos. are 3598122, 4144317, 4201211, 4262003 and 4379454, for example, which patents are hereby incorporated by reference herein. The simplest type of a transdermal delivery system comprises an agent reservoir which may be merely a mixture of a matrix material containing dissolved or dispersed agent which is maintained on the skin for a predetermined period of time by an adhesive or other means such as a strap. Matrix systems have the advantage of being easily fabricated and are generally of lower cost than more sophisticated rate controlled systems. The rate of release of an agent from a matrix however decreases as a function of $t^{-\frac{1}{2}}$. This type of decline in release rate occurs when the agent is included in the matrix at a concentration above the saturation concentration of the agent in the matrix and becomes even more pronounced (e.g., exponential) when the agent in the supersaturated reservoir falls below saturation or is originally incorporated in the matrix at or below the saturation concentration.

For this reason it is generally desired to fabricate transdermal delivery systems with a sufficient amount of excess agent in the matrix to maintain the matrix at unit activity (or saturation) for a substantial portion of its useful life. In addition to the use of release rate controlling elements to make the release rate more constant with time, various approaches to improving the release characteristics from simple matrix type systems have been proposed. See for example, U.S. Pat. Nos. 3923939 and 4286592, which patents are incorporated herein by reference.

In certain circumstances, however, it is not only unnecessary to maintain the drug reservoir above saturation during its useful life but it is actually undesirable to do so. For example, with expensive agents it would be desirable to keep the residual agent left in the system after use to a minimum. In the case of a system in which unit activity is maintained throughout its useful life, however, the residual agent would never be present at less than the saturation concentration of the agent in the reservoir. Similarly, it is not always desirable to have a relatively constant agent input particularly when one is attempting to mimic normally fluctuating blood levels of an endogenously produced agent such as in hormone supplementation therapy or insulin administration. In these situations the normal blood levels of the agent fluctuate from a high level to a low level over various body cycle periods and agent administration would desirably parallel normal blood level cycling. The release rate from a subsaturated matrix, characterized by an initially high release rate which rapidly decays may, nevertheless, be unsuitable for even these applications and it would be desirable to provide some way for flattening out the release curve and extending the useful life of a substituted system. As used herein the term "subsaturated" shall refer to a matrix which is substantially free from any dispersped, undissolved agent and includes a matrix in which the agent may initially be at the saturation level prior to use.

According to our invention we have devised a transdermal therapeutic system employing a subsaturated agent reservoir having improved agent release characteristics. We have also provided transdermal therapeutic systems which are particularly adapted for administration of androgens such as testosterone, progestins such as estradiol, steroids such as hydrocortisone and antiviral agents such as acyclovir for example. We have also provided a transdermal therapeutic system which is particularly adapted for scrotal and labial administration of drugs.

Accordingly, it is an object of this invention to provide an improved transdermal therapeutic system utilizing a subsaturated reservoir.

It is another object of this invention to provide a transdermal therapeutic system particularly adapted for scrotal or labial delivery of drugs.

It is another object of this invention to provide a simple, inexpensive transdermal therapeutic system having improved release characteristics.

These and other objects of the invention will be readily apparent from the following description with reference to the accompanying drawing wherein.

DESCRIPTION OF THE INVENTION

Figure 1:
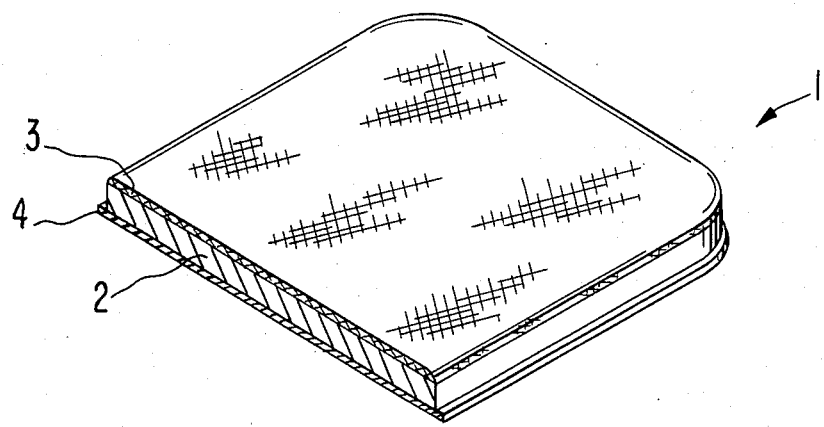
FIG. 1 represents a cross-section through a perspective view of one embodiment of this invention.
Figure 2:
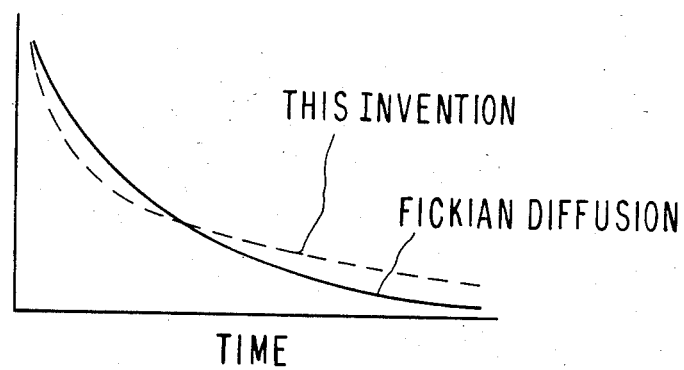
FIG. 2 is a plot of theoretical in vitro release rate vs. time comparing transdermal therapeutic systems of this invention with the prior art.

In its simplest form, a transdermal therapeutic system 1 according to this invention is shown in FIG. 1. Such a system 1 comprises a drug reservoir 2 typically in the form of an aqueous or non-aqueous gel or polymeric material having the agent to be delivered dissolved therein at a concentration no greater than the saturation concentration of the agent in the matrix material. If necessary the matrix may also contain skin permeation enhancers, stabilizing agents carriers or other additives as is known to the art.

In the embodiment shown in FIG. 1, no additional adhesive or attaching means is provided because the matrix material has been selected to have sufficient tack to maintain the system in close contact to the skin at the situs of use. In other systems, adhesive overlays or substrates or belts or buckles would be employed.

In order to strengthen the reservoir 2, facilitate handling, application and removal of the device and to provide protection of the body distal portion of the device, the body distal surface is provided with reinforcing means 3, typically in the form of woven or non-woven relatively open mesh fabric, chemically inert with respect to other components of the system, embedded in the upper surface of device 1. An impermeable release liner 4, adapted to the easily removed from the body contacting surface of the drug reservoir 2 prior to use would normally be provided to protect the system in its package.

According to our invention at least a portion of the reinforcing means 3 is formed from a material having a discrete, measurable solubility, $C_r$, for the agent to be dispensed which solubility is no greater than the initial concentration, $C_o$, of the agent in the matrix material 2 and a diffusion coefficient $D_e$ for the agent which is selected with respect to the diffusion coefficient of the agent in the matrix, $D_m$ such that the following relationship exists:

$$C_r \cdot D_r < D_m \cdot C_o \qquad (1)$$

This results in a prolongation of the effective dispensing life of the system 1 and a flattening of the release rate curve. This occurs because the portion of the reinforcing means containing the dissolved agent tends to act as a secondary reservoir for the agent which continues to release agent after the concentration of the agent in the matrix has been reduced to the concentration in the reinforcing means as a result of the transfer of the agent from the matrix 2 into the skin.

Expressed mathematically, the initial release rate from the matrix will be governed by Fick's second law:

$$\frac{dM_t}{dt} = M_\infty \left( \frac{D_m}{\pi l^2 t} \right)^{\frac{1}{2}} \quad (2)$$

in which $M_\infty$ is the initial mass of agent, $D_m$ is the diffusion coefficient of the agent in the matrix, l is the thickness of the matrix and t is time. After a certain time, the release rate from a simple matrix system is theoretically governed by:

$$\frac{dM_t}{dt} = \frac{8 D_m M_\infty}{l^2} \exp\left( \frac{-\pi^2 D_m t}{l^2} \right) \quad (3)$$

However, according to our invention, after partial depletion of the agent from the matrix the latter stage of release will be determined by the secondary reservoir which has a pseudo-steady state release rate governed by:

$$\frac{dM_t}{dt} = \frac{DC_r}{l} \quad (4)$$

in which $C_r$ is the concentration (or solubility) of the agent in the secondary reservoir formed from at least portion of the reinforcing means and the remaining symbols have meanings shown above.

These relationships are represented graphically in FIG. 2 wherein the theoretical in vitro release of agent from a subsaturated matrix into an infinite sink is shown in solid lines and a typical release pattern obtained according to this invention wherein at least a portion of the reinforcing means has the required solubility for the agent is shown in dotted lines.

The extent of departure from the theoretical release rate can be varied by adjustment of various parameters of the system Although absolute values of the solubility and the diffusion coefficients of the agent in the reinforcing means and the matrix are not critical, the products of $D_r$ and $C_r$ should be less than the products $D_m$ and $C_o$ by at least 10% and preferably about 100%. The greater the percentage of the overall device which is comprised of the agent solvent portion of the reinforcement means, the more pronounced will be the effect for a given difference in the D·C values. Thus, by appropriate selection of the initial concentration and diffusion coefficients of the agent in the matrix, the solubility and the diffusion coefficient of the agent, in the reinforcing means, and the relative proportions of the materials in the overall device a high degree of design flexibility is available in obtaining a desired release rate pattern.

It should be noted that the reinforcing means need not be fabricated entirely from a material having the desired degree of solubility for the agent. For example, in a typical reinforcement means, spun-bonded polyester fabric, the individual polyester fibers are coated with a polyolefinic bonding agent or heat sealable material such as polyethylene, which bonds the individual fibers into a fabric. In a preferred embodiment of this invention the agent is soluble in the polyethylenic bonding agent while not being soluble in the reinforcing fiber per se.

Suitable matrices for the fabrication of the reservoir can be selected from a wide variety of materials known to the art as noted in the U.S. Patents cited above and include, without limitation, natural and synthetic polymers such as natural or synthetic rubbers, low density polyethylene and ethylene vinylacetate (EVA) polymers such as are disclosed for example in U.S. Pat. Nos. 4069307 and 4144317; aqueous based systems comprising aqueous reservoirs gelled with carboxy methylcellulose, collodial silicon dioxide or any of a wide variety of other gelling agents known to the art. The poor adhesive properties of aqueous gels generally require the use of an adhesive overlay or a belt or buckle to maintain the system in contact with the skin.

Suitable reinforcing means include spun bonded polyester and polyamide fabric such as noted above as well as natural or synthetic woven fabrics, and chopped rovings which may, in any case, be coated with an appropriate material having the desired solubility characteristics for the particular agent and matrix with respect to which it is incorporated. Since the fibers themselves need not have the necessary solubility characteristics it is only necessary to coat the fibers or impregnate the fabric with a material having desired solubility in order to produce the desired results according to this invention.

Preferred embodiments of this invention are particularly adapted for the scrotal and labial administration of various drugs such as testosterone and progesterone. Progesterone and testosterone are known to be absorbable through the skin and both testosterone and progesterone have been so administered. Ben Galim, et al., "Topically Applied Testosterone and Phallic Growth", Am. J. Dis. Child. 134: 296–298 (1980), Jacobs, et.al. Topical Testosterone Therapy for Penile Growth. Urol. 6: 708–710 (1975), and Klugo, et al., "Response of Micropenis to Topical Testosterone and Gonadotropin", J. Urol, 119: 667–668 (1978) report that the application of 5 and 10 percent testosterone cream either on the penis or axilar skin of children with microphallus has stimulated phallic growth and elevated serum testosterone levels. An alcoholic gel sold in 100 mg. dosages for application three times a week is also available in France under the trade name Percutacraine Androgenique Forte manufactured by Besins-Iscoveseo for testosterone replacement.

Goldzieher, et al., "The Percutaneous Absorption of Estradiol-17B and Progesterone" report the percutaneous absorption of progesterone from an ointment base.

Transdermal delivery systems for administering testosterone or progesterone according to this invention comprises an approximately 35 cm² rectangular patch with rounded corners which is designed to release approximately 5 mg of the drug over a 24 hour period. The patches are intended to be applied either to the scrotum or labia and left in place for up to 24 hours or such shorter period as may be required to obtain the desired blood levels for a particular individual. The scrotal and labial delivery routes are preferred because of the high permeability of scrotal and labial tissue. The psychological effect of the scrotal delivery site when testosterone deficiency has resulted in sexual dysfunction is also a factor in selection.

The sensitivity of scrotal and labial tissue and their irregular configurations imposes significant constraints on the characteristics that a transdermal system for scrotal or labial administration of drugs must have. For example, the system must be sufficiently thin and flexible so as to be able to easily conform to the configuration of the labia or the scrotal sack and must be sufficiently adherent to be able to maintain itself in place without being so adherent as to create discomfort on removal. For such applications we have determined that the thickness of the system should be in a range from approximately 2 mil to approximately 10 mil with 3 to 5 mil being preferred. The peel strength of the skin contacting surface should be sufficiently high to maintain contact during use and sufficiently low to be removable without pain or irritation. Peel strengths in the range of 1-20 gm/cm are contemplated. EVA polymers having from 40% to 60% vinyl acetate exhibit a satisfactory combination of tack, solubility and diffusivity for use with drugs such as testosterone and progesterone, for example.

EXAMPLE 1

Figure 3:
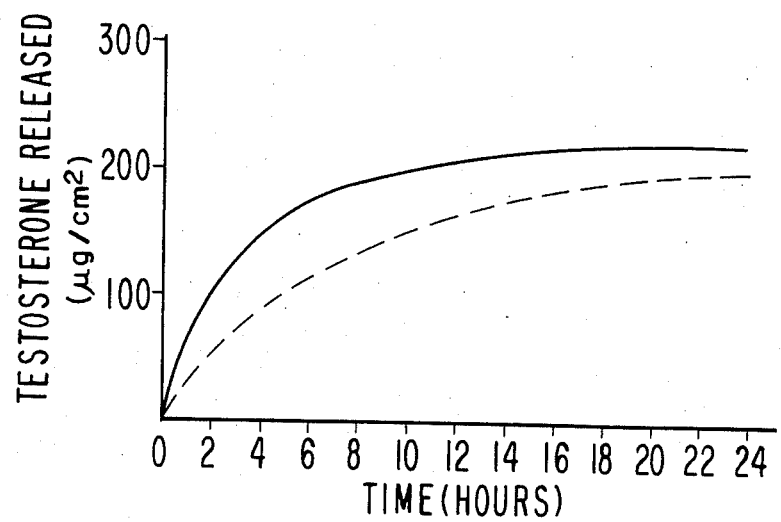
FIG. 3 is a plot comparing theoretical in vitro agent release to the actual agent release observed with an embodiment of this invention.

A solution of 24.38% EVA (51% VA) dissolved in methylene chloride to which was added 0.625% testosterone was mixed until dissolution occurred. The solution was then solvent cast as a 3 mil film onto an impermeable release liner and the solvent evaporated to yield a material comprising 97.5% EVA and 2.5% testosterone. A spun bond polyester fabric, ½ oz/yd², sold by Chicopee Mills as fabric Code No. 9123 was applied over the approximately 3 mil thick EVA layer. The test sample was thereafter die cut to 35 sq.cm. corners approximately 5×7 cm in each dimension, in the process of which the spun bond polyester fabric was embedded in the upper surface of the EVA layer. The systems were allowed to sit for at least 48 hours during which time the testosterone dissolved in the polyethylenic bonding agent applied to the polyester fibers in the manufacture of the spun bond fabric. The in vitro testosterone release rate v. time profile into an infinite sink from the system so fabricated compared to the theoretical release from a simple matrix is shown in FIG. 3.

EXAMPLE 2

After removal of the impermeable release liner, transdermal delivery systems produced according to Example 1 may be applied to the scrotum of a testosterone deficient male prior to retiring and left in place for between 8 and 24 hours depending on the cyclical testosterone blood level desired for testosterone replacement therapy. After initial application new systems may be applied immediately or after a predetermined time as a means of chronic therapy. The system of Example 1 may also be applied to the skin of the thigh or other relatively hair free portion of the body to produce similar results.

EXAMPLE 3

A progesterone loaded system was prepared by the process described in Example 1 with progesterone being substituted for the testosterone. Two of the rectangular 35 cm² patches were applied to intact skin of human subject, blood samples were taken and assayed for progesterone content at various times. The results compared to base line levels are shown in Table 1.

TABLE I

| Date   | Time   | Progesterone Blood Level (units) |
|--------|--------|----------------------------------|
| Day 1  | 8:53   | 34 ng/dl                         |
| Day 1  | 11:45  | 33 ng/dl                         |
| Day 23 | 8:15*  | 37 ng/dl                         |
| Day 23 | 10:22  | 156 ng/dl                        |
| Day 23 | 12:22  | 191 ng/dl                        |
| Day 23 | 16:09  | 176 ng/dl                        |
| Day 24 | 7:00xx |                                  |
| Day 24 | 8:57   | 53 ng/dl                         |

*System Applied
**System Removed

EXAMPLE 3

A transdermal therapeutic system containing hydrocortisone is fabricated by solvent casting from methylene chloride in the form of a 10 mil thick Kraton 2104 styrene-butadiene block copolymer available from Shell Chemical Company containing 0.27 weight percent of hydrocortisone. Nomex heat-resistant aromatic polyarylamide fiber available from DuPont Chemical Company is pressed into the upper surface of the Kraton film and die cut into 35 sq² rectangular patches with rounded edges each containing 2.4 mil of hydrocortisone. The diffusion coefficient and saturation concentration of the hydrocortisone in the matrix and backing material are shown in Table 2. The systems are allowed to sit for at least 48 hours to allow the hydrocortisone to equilibriate between the matrix and Nomex backing. The systems are preferably applied to intact skin for transdermal delivery of hydrocortisone.

TABLE 2

| Material    | D (cm²/sec)         | $C_s$ (μg/cm³) | D $C_s$ (μg/cm/sec)  |
|-------------|---------------------|----------------|----------------------|
| Nomex       | $3 \times 10^{-9}$  | 2000           | $6 \times 10^{-6}$   |
| Kraton 2104 | $1 \times 10^{-10}$ | 3000           | $3 \times 10^{-10}$  |

This invention has been described with respect to certain specific embodiments but it should not be construed as being limited thereto. Various modifications will suggest themselves to workers skilled in the art which can be made without departing from the scope of this invention which is limited only by the following claims wherein:

We claim:

1. A subsaturated transdermal therapeutic system having improved release characteristics comprising, in combination:

(a) a matrix containing an active agent to be dispensed therefrom at an initial concentration, $C_o$, no greater than the saturation concentration of the agent in the matrix;

(b) reinforcing means within the matrix, at least a portion of said reinforcing means being a solvent for said agent, said portion of said reinforcing means having a solubility for said agent, $C_r$, less than the initial concentration of the agent in the matrix and wherein the diffusion coefficient of said agent in said matrix is $D_m$, the diffusion coefficient of said agent in the solvent portion of said reinforcing means is $D_r$ and the values of $D_m$, $D_r$, $C_o$ and $C_r$ are selected such that:

$$D_r C_r < D_m \cdot C_o.$$

2. The transdermal therapeutic system of claim 1 wherein $D_r \cdot C_r$ is at least 10% less than $D_m \cdot C_o$.

3. The transdermal therapeutic system of claim 2 wherein said reinforcing means comprises a fabric imbedded in the body distal portion of the system.

4. The transdermal therapeutic system of claim 3 wherein the overall thickness of said system is in the range of from about 2-10 mils.

5. A transdermal therapeutic system according to claim 1 particularly adapted for application to sensitive skin surfaces for an extended time period wherein said reinforcing means comprises fibrous means imbedded in the body distal surface of said matrix and said matrix is adherent to said sensitive skin surfaces with a peel strength sufficiently high to maintain said system in place for said extended time period and sufficiently low to be removed without discomfort.

6. The system of claim 5 wherein the peel strength of said material from skin is in the range of 1-20 gm/cm.

7. The system of claim 5 wherein the overall thickness of the system is in the range of 2-10 mils.

8. The system of claim 7 wherein said agent is selected from the group consisting of testosterone and progesterone and and said matrix comprises an ethylene/vinyl acetate copolymer containing from about 40 to 60% vinyl acetate and said system is from about 2-10 mils thick.

9. A method of transdermal administration of an agent which comprises applying a system according to claim 7 to the scrotum of a male subject or the labia of a female subject and maintaining said system in place for an extended period of time.

10. A method of transdermal administration of an agent which comprises applying a system according to claim 8 to the scrotum of a male subject or the labia of a female subject and maintaining said system in place for an extended period of time.

11. The transdermal therapeutic system of claim 1 wherein said reinforcing means comprise fibrous reinforcing means.

12. The transdermal therapeutic system of claim 11 wherein said fibrous reinforcing means are imbedded in the skin distal surface of said matrix.

13. The transdermal therapeutic system of claim 11 wherein the solvent portion of said reinforcing means is a coating on the fibers forming said reinforcing means.

14. The transdermal therapeutic system of claim 12 wherein the solvent portion of said reinforcing means is a coating on fibers forming said reinforcing means.

15. This system according to claim 8 wherein said agent is testosterone.

16. The system of claim 8 wherein said agent is progesterone.

17. The transdermal therapeutic system of claim 8 wherein said reinforcing means comprises fibrous reinforcing means.

18. The transdermal therapeutic system of claim 17 wherein said fibrous reinforcing means are imbedded in the skin distal surface of said matrix.

19. The transdermal therapeutic system of claim 18 wherein the solvent portion of said reinforcing means is a coating on the fibers forming said reinforcing means.

20. A transdermal therapeutic system particularly adapted for application to sensitive skin surfaces for an extended time period comprising, in combination:
   (a) a matrix containing an active agent to be dispensed therefrom at an initial concentration, $C_o$, no greater than the saturation concentration of said agent in the matrix and having a diffusion coefficient of said agent in said matrix, $D_m$;
   (b) fibrous reinforcing means imbedded in the body distal surface of said matrix, at least the exterior portion of said fibrous reinforcing means being a solvent for said agent having a solubility for said agent, $C_r$, less than $C_o$, and having a diffusion coefficient for said agent in said portion, $D_r$;
   (c) said agent, matrix and exterior portion of said fibrous reinforcing means are selected such that:

$$D_r C_r < D_m \cdot C_o;$$

and
   (d) said matrix being adherent to said sensitive skin surface with a peel strength sufficiently high to allow said system to remain in place for said extended time period and sufficiently low to the removed without discomfort.

21. The transdermal therapeutic system of claim 20 wherein $D_r \cdot C_r$ is at least 10% less than $D_m \cdot C_o$.

22. The transdermal therpeutic system of claim 20 wherein the overall thickness of said system is in the range of 2-10 mils.

23. The transdermal therapeutic system of claim 20 wherein said matrix is selected from the group consisting of ethylene/vinyl acetate copolymer, natural rubbers, synthetic rubbers, and low density polyethylene.

24. The transdermal therapeutic system for claim 21 wherein said exterior portion of said reinforcing means is selected form the group consisting of polyolefins and polyarylamides.

25. The transdermal therapeutic system of claim 22 wherein said agent is selected from the group consisting of progesterone, testosterone and hydrocortisone.

26. The transdermal therapeutic system of claim 23 wherein said matrix is selected from the group consisting of ethylene/vinyl acetate copolymers and styrene-butadiene block copolymers, said exterior portion of said reinforcing means is selected from the group consisting of polyolefins and polyarylamides.

27. The transdermal therapeutic system of claim 26 wherein said agent is selected from the group consisting of progesterone, testosterone and hydrocortisone.

28. The transdermal therapeutic system of claim 26 wherein said matrix is an ethylene/vinyl acetate copolymer and said exterior portion of said reinforcing means is polyethylene.

29. The transdermal therapeutic system of claim 26 wherein said matrix is a styrene-butadiene block copolymer and said exterior portion of said reinforcing means is a polyarylamide.

30. The transdermal therapeutic system of claim 27 wherein said matrix is an ethylene/vinyl acetate copolymer and said exterior portion of said reinforcing means is polyethylene.

31. The transdermal therapeutic system of claim 27 wherein said matrix is a styrene-butadiene block copolymer and said exterior portion of said reinforcing means is a polyarylamide.

32. The transdermal therapeutic system claim 30 wherein said agent is progesterone.

33. The transdermal therapeutic system of claim 30 wherein said agent is testosterone.

34. The transdermal therapeutic system of claim 31 wherein said agent is hydrocortisone.

35. The transdermal therapeutic system of claim 8 wherein said agent is testosterone.

36. The transdermal therapeutic system of claim 1 wherein said agent is testosterone.

37. A method for testosterone replacement in hypogonadic males which comprises applying the system of claim 35 to the scrotum of a hypogonadic male and maintaining said system in testosterone transfering relationship to said scrotum for at least about 8 hours.

38. A method for testosterone replacement in hypogonadic males which comprises applying the system of claim 36 to the scrotum of a hypogonadic male and maintaining said system in testosterone transfering relationship to said scrotum for at least about 8 hours.

39. The method of claim 37 wherein said system is maintained in place for about 24 hours and is replaced with a fresh system upon removal whereby continuous testosterone replacement is obtained.

40. The method of claim 38 wherein said system is maintained in place for about 24 hours and is replaced with a fresh system upon removal whereby continuous testosterone replacement is obtained.

41. The system of claim 20 wherein said agent is testosterone and said matrix is an ethylene/vinyl acetate copolymer having from about 40%-60% vanyl acetate.

42. A method for testosterone replacement in hypogonadic males which comprises applying the system of claim 41 to the scrotum of a hypogonadic male and maintaining said system in testosterone transfering relationship to said scrotum for at least about 8 hours.

43. The method of claim 42 wherein said system is maintained in place for about 24 hours and is replaced with a fresh system upon removal whereby continuous testosterone replacement is obtained.

* * * * *

UNITED STATES PATENT AND TRADEMARK OFFICE
CERTIFICATE OF CORRECTION

PATENT NO. : 4,704,282

DATED : November 3, 1987

INVENTOR(S) : Patricia S. Campbell, James B. Eckenhoff

It is certified that error appears in the above-identified patent and that said Letters Patent is hereby corrected as shown below:

In Item [75] Inventors, add --Virgil A. Place, Kawaihae, Hawaii--; column 2, line 1, "substituted" should be --subsaturated--; column 2, line 3, "dispersped" should be --dispersed--; column 2, line 65, "the" should be --be--; column 3, line 52, insert --a-- before "portion"; column 5, line 51, insert --major-- after "each"; column 6, line 29, "Example 3" should be --Example 4--; column 6, line 39, "sq$^2$" should be --cm$^2$--; column 7, line 36, delete "and" (second occurrence); column 8, line 30, "the" should be --be--; column 8, line 43, "form" should be --from--; column 9, line 19, "transfering" should be --transferring--; column 10, line 1, "transfering" should be --transferring--; column 10, line 13, "vanyl" should be --vinyl--; column 10, line 17, "transfering" should be --transferring--.

Signed and Sealed this

Twenty-second Day of November, 1988

Attest:

DONALD J. QUIGG

*Attesting Officer*   *Commissioner of Patents and Trademarks*